US012773576B2

(12) United States Patent
Otto et al.

(10) Patent No.: US 12,773,576 B2
(45) Date of Patent: Oct. 27, 2026

(54) RADIATION THERAPY TREATMENT PLANNING USING NODE-BASED FUNCTIONS FOR UPDATING TARGET VOLUMES

(71) Applicant: Radformation, Inc., New York, NY (US)

(72) Inventors: Karl Otto, New York, NY (US); Artur Karlov, New York, NY (US); Jonathan Giambattista, New York, NY (US)

( * ) Notice: Subject to any disclaimer, the term of this patent is extended or adjusted under 35 U.S.C. 154(b) by 268 days.

(21) Appl. No.: 18/828,832

(22) Filed: Sep. 9, 2024

(65) Prior Publication Data

US 2025/0082965 A1 Mar. 13, 2025

Related U.S. Application Data

(60) Provisional application No. 63/537,302, filed on Sep. 8, 2023.

(51) Int. Cl.
*A61N 5/10* (2006.01)
*G16H 20/40* (2018.01)
*G16H 30/40* (2018.01)

(52) U.S. Cl.
CPC ......... *A61N 5/1031* (2013.01); *A61N 5/1071* (2013.01); *G16H 20/40* (2018.01); *G16H 30/40* (2018.01); *A61N 2005/1035* (2013.01); *A61N 2005/1074* (2013.01)

(58) Field of Classification Search
CPC ................ A61N 5/1031; A61N 5/1071; A61N 2005/1035; A61N 2005/1074; A61N 5/103; G16H 20/40; G16H 30/40
See application file for complete search history.

(56) References Cited

U.S. PATENT DOCUMENTS 7,831,289 B2 * 11/2010 Riker ..................... G16H 70/20 378/65
10,835,759 B2 * 11/2020 Chiu .................... A61N 5/1031
11,083,911 B2 * 8/2021 Joe Anto .............. A61N 5/1039
11,278,737 B2 * 3/2022 Peltola .................... G06F 17/10
11,986,677 B2 * 5/2024 Smith .................. A61N 5/1049
12,011,613 B2 * 6/2024 Peltola ................. A61N 5/1031
12,086,391 B2 * 9/2024 Vojan ................... A61N 5/1048
12,115,392 B2 * 10/2024 Brown ................. A61N 5/1049
12,251,575 B2 * 3/2025 Peltola ................. A61N 5/1031
12,296,192 B2 * 5/2025 Chen ....................... A61N 5/103
12,324,930 B2 * 6/2025 Peltola ................. A61N 5/1031
12,508,444 B2 * 12/2025 Kuusela ............... A61N 5/1038
12,515,074 B2 * 1/2026 Jia .......................... A61N 5/103
RE50,811 E * 3/2026 Fahrig .................. A61N 5/1039
12,642,991 B2 * 6/2026 Stanchev .............. A61N 5/103
(Continued)

*Primary Examiner* — Kenny Nguyen

(57) ABSTRACT

The system and method provided herein is an interactive computer based graphical user interface that permits a user to dynamically assemble, and process, spatially contoured (segmented) anatomical structures shown on medical images for radiation treatment planning. The generation of planning structures utilizing node-based operations based on contoured organs is a critical part of the radiation therapy planning workflow. The overall goal is to optimize the plan for treatment and deliver a precise dose of radiation to a target (typically a tumor) while minimizing radiation exposure to surrounding healthy tissues.

10 Claims, 6 Drawing Sheets

(56) References Cited

U.S. PATENT DOCUMENTS 12,646,596 B2 * 6/2026 Khuntia ................. A61N 5/103
2004/0068182 A1 * 4/2004 Misra ................... A61N 5/1049
600/427
2004/0264640 A1 * 12/2004 Myles .................... G16H 50/50
378/65
2005/0111621 A1 * 5/2005 Riker ..................... G16H 20/40
378/65
2007/0201614 A1 * 8/2007 Goldman ............... G16H 20/40
378/65
2010/0183121 A1 * 7/2010 Riker ..................... G16H 70/20
378/65
2018/0157928 A1 * 6/2018 Oliveira ................. G16H 30/40
2018/0214713 A1 * 8/2018 Dehghan Marvast . A61B 8/085
2018/0242917 A1 * 8/2018 Bagherzadeh ....... A61B 5/0263
2019/0070435 A1 * 3/2019 Joe Anto ................ A61N 5/103
2019/0189292 A1 * 6/2019 Shaya .................... G16H 80/00
2020/0001112 A1 * 1/2020 Chiu ...................... A61N 5/103
2020/0030632 A1 * 1/2020 Munbodh ............ A61N 5/1071
2020/0286601 A1 * 9/2020 Khuntia ................. A61N 5/103
2021/0069527 A1 * 3/2021 Peltola ................. A61N 5/1075
2021/0192719 A1 * 6/2021 Laaksonen ........... G06N 3/0895
2022/0161058 A1 * 5/2022 Peltola ................. A61N 5/1031
2022/0161062 A1 * 5/2022 Adamson ............... G16H 40/63
2022/0206648 A1 * 6/2022 Vojan ..................... G16H 30/20
2022/0288420 A1 * 9/2022 Brown ................. A61N 5/1037
2022/0296926 A1 * 9/2022 Kolesnick ............ A61N 5/1031
2022/0323793 A1 * 10/2022 Brooks .................. A23B 4/015
2023/0111230 A1 * 4/2023 Chen ...................... A61N 5/103
600/1
2023/0405356 A1 * 12/2023 Peltola ................. A61N 5/1031
2024/0001145 A1 * 1/2024 Passerini ................ A61N 5/103
2024/0042240 A1 * 2/2024 Stanchev ............... A61N 5/103
2024/0104767 A1 * 3/2024 Voronenko ............. A61N 5/103
2024/0226603 A1 * 7/2024 Peltola ................. A61N 5/1031
2025/0050133 A1 * 2/2025 Kuusela ............... A61N 5/1038

* cited by examiner

200

RADIATION THERAPY TREATMENT PLANNING USING NODE-BASED FUNCTIONS FOR UPDATING TARGET VOLUMES

CROSS-REFERENCE TO RELATED APPLICATION

This application claims the benefit of U.S. Provisional Application No. 63/537,302, filed Sep. 8, 2023 and entitled "System and method for radiation therapy treatment planning".

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Radiation-treatment plans typically serve to specify any number of operating parameters as pertains to the administration of such radiation dose with respect to a given patient. For example, many treatment plans provide for exposing the target volume to possibly varying doses of radiation from several different directions.

The development of such plans typically comprises a multi-step process. This can include, for example, acquiring or otherwise accessing patient information, defining structures of interest (regarding, for example, the treatment target, adjacent organs, and so forth), creating a field setup, optimizing a treatment plan, calculating a treatment dose (or doses), evaluating and approving the plan, and scheduling the corresponding treatment. Accordingly, the development of such a plan (or plans) often comprises a lengthy process. Such temporal considerations do not always match the needs of patients, treatment planners, technicians, administrators, and other interested parties.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
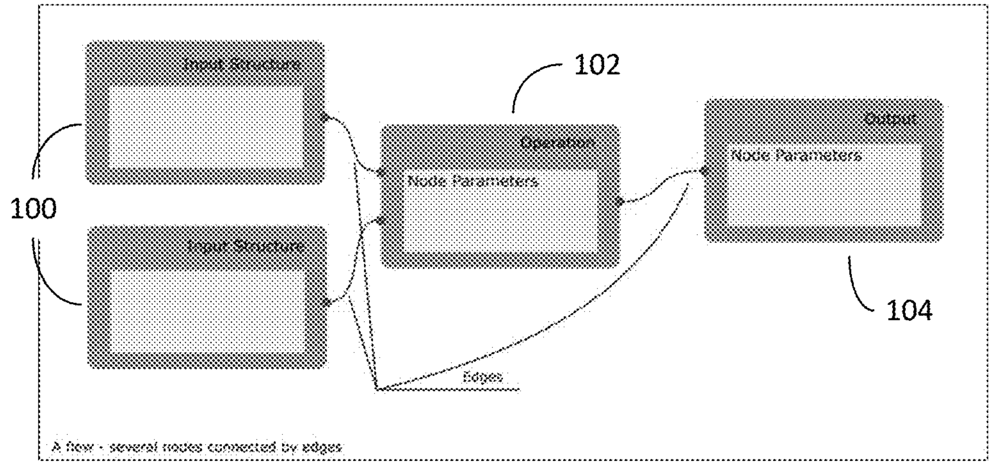
FIG. 1 is a process flow diagram of the edge node creation elements consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

It is noted in particular that where a range of values is provided in this specification, each value between the upper and lower limits of that range is also specifically disclosed. The upper and lower limits of these smaller ranges may independently be included or excluded in the range as well.

The invention is an interactive computer based graphical user interface that permits a user to dynamically assemble, and process, spatially contoured (segmented) anatomical structures shown on medical images.

The generation of planning structures based on contoured organs is a critical part of the radiation therapy planning workflow. The overall goal is to deliver a precise dose of radiation to a target (typically a tumor) while minimizing radiation exposure to surrounding healthy tissues. Here is a general overview of the process, although it's important to note that specifics can vary based on the software and equipment being used, as well as the complexity of the case.

In an embodiment the initial imaging and diagnosis includes acquiring a set of imaging data through the usual modalities such as Computer Tomography (CT), Magnetic Resonance Imaging (MRI), or Positron emission tomography (PET) scans. Upon acquiring the set of imaging data through one or more of the indicated scan modalities, the imaging data set is provided to one or more radiologist and/or radiation oncologists. The radiologist(s) and/or radiation oncologist(s) review the set of imaging data to identify critical structures, organs, and/or tumors, if such tumors are present and visible within the imaging data.

Radiation oncologists may then draw contours around Organs-At-Risk (OARs) on the images present in the imaging data set. OARs are defined as healthy organs and tissues that could potentially be harmed by radiation during any radiation treatment action. Additionally, contours may also be drawn around the Gross Tumor Volume (GTV), Clinical Tumor Volume (CTV), and the Planning Target Volume (PTV). These parameters define the tumor and the region for which radiation treatment is indicated and required.

In an embodiment, Machine Learning (ML) and Artificial Intelligence (AI) based algorithms may be used to create a method to increase the speed with which radiation treatment regions within the imaging data set are identified and contours of the region generated. The ML and/or AI methods may use deep learning and one or more trained data sets to generate planning structures based upon learned patterns in the training data that have been reviewed and approved by one or more radiologists and/or radiation oncologists. The system may also employ a random forest methodology which is an ensemble learning method that utilizes multiple decision trees to vote on the contour or structure. A random forest methodology may be employed to increase confidence in the marked treatment locations within the imaging data. A majority vote is required when utilizing a random forest methodology to verify the area of the imaging data to be marked for treatment.

Alternatively, or in addition, an atlas-based methodology may be utilized that uses a database of previously contoured images to inform the structure generation on new images, once again increasing the confidence in identification and extent of the area that is subject to radiation treatment therapy.

In an embodiment, hybrid methods may be employed to mark a treatment area within the imaging data. A semi-automatic hybrid may provide automatic contour generation of the treatment area in an initial operation and the generated contour of the treatment area is then manually edited by a radiologist or radiation oncologist to further refine the treatment area. Alternatively, an iterative refinement method may be used where the ML or AI algorithm generates initial structures, a radiologist or radiation oncologist inputs corrections to structures and another iteration of the structure generation is performed. These steps may be iteratively performed until the radiologist or radiation oncologist has confidence that the generated structures are as accurate as possible given the data within the imaging data set. The generated structure set is then accepted and used for the generation of a therapy treatment plan.

In an embodiment, specialized methods such as functional imaging or multi-modality fusion may be employed to generate planning structures. In functional imaging the system uses advanced imaging techniques such as diffusion MRI or dynamic contrast-enhanced MRI to guide the contouring for the planning structures and generate planning structures having a higher degree of confidence in the accuracy of the generated structures. In multi-modality fusion the system may utilize more than one type of imaging, such as, in a non-limiting example, a combination of CT and MRI modalities, to generate more accurate or specialized planning structures.

In an embodiment, planning structures for the treatment area may be generated that expand on the original contours. In a non-limiting example, the contour expansion may be achieved by adding a margin to the CTV to create the PTV. This margin expansion may account for potential errors in the imaging scan data and/or account for patient movement during scan capture of the imaging scan data. Additionally, planning structures may be refined utilizing Boolean operations (such as union, intersection, subtraction, and other Boolean operations) between different contours. In a non-limiting example, a planning operation might subtract an OAR from a PTV to ensure that the OAR receives a lower dose of radiation to minimize damage to the OAR. In other operations derived structures may be generated that are based upon existing contours as defined within the imaging data. These derived structures may include items like dose-limiting shells around OARs or expanded PTVs for radiation dose gradients.

In each case planning structures may be generated in two dimensions or three dimensions based upon the application of the appropriate algorithm.

Dose Planning may begin once planning structures have been generated and approved by the radiologist or radiation oncologist. A Treatment Planning System (TPS) may use one or more algorithms to optimizes the radiation dose delivery based upon the generated planning structures and any specialized considerations that impact the generation of the TPS or planned dosage. In a non-limiting example, the TPS takes into account dose-volume constraints to ensure that radiation exposure to OARs is minimized.

Prior to any treatment being enacted, the entire team involved in the planning and delivery of radiation treatment reviews the dose plan to ensure that the generated dose plan meets clinical criteria for the therapy to be performed. Additionally, dosimetric verification analysis may be performed through the use of physical tests or computer simulations to verify that the plan may be accurately delivered by the treatment machine to be used to deliver the radiation dose according to the dose plan.

Upon approval of the treatment plan the treatment team is involved in actually delivering the approved treatment to the patient according to the targeted area and utilizing the determined doses of radiation. The patient is positioned using immobilization devices and, frequently, a confirmation initial image is captured to confirm alignment of the treatment area with the treatment machine. The radiation dose is then delivered according to the approved treatment plan, subject to any adaptive planning that may be required to accommodate changes in the patient's anatomy or tumor size.

Throughout this process, specialized software is often used for contouring, planning structure generation, and dose planning. This software can vary in its complexity and capabilities, but the basic aim is always to achieve at least a minimum dose to the tumor while minimizing the dose to healthy tissues.

Node-based interfaces are novel to the process of generating planning structures for radiation therapy. In radiation therapy planning, various methods, options and interfaces exist for generating planning structures based on contoured organs and target volumes. The methods can range from straightforward expansions to more complex derived structures.

The system utilizes a node-based interface to create both treatment planning volumes and treatment plans. In an embodiment, nodes may represent different actions or tasks that may be utilized to manage complex workflows, processes, or data pipelines by connecting different "nodes" together. This type of interface is highly interactive, enabling the encapsulation of functions, operations, or tasks within nodes that can be visually connected to define a flow of data or control.

Types: Nodes usually come in various types, each representing a different function, operation, or task (e.g., data import, data export, data transformation, visualization, etc.).

Ports: Each node typically has input and output ports. Input ports receive data or control signals, while output ports send data or control signals.

Properties/Parameters: Each node often has its own set of customizable properties or parameters, allowing users to fine-tune its behavior.

Connection lines within the GUI may be the lines that connect the output port of one node to the input port of another, establishing the flow of data or control.

Connection lines can sometimes be directional or bidirectional, and in some systems, they may carry different types of data (e.g., numerical, textual, boolean).

In an embodiment a GUI canvas presents the main area where nodes and edges are displayed. It's often a large, scrollable, and zoomable space. Users can typically drag nodes from a sidebar into this workspace or add them directly without leaving the canvas and then draw connections between them.

The toolbar may contain a list of available nodes that users can drag into the workspace. The toolbar may also have other tools for managing the view, such as zooming or fitting the canvas, and options for saving or loading workflows.

In an embodiment the node-based interface supports drag-and-drop functionality for both nodes and connections. The system may also offer real-time feedback, allowing users to see immediate results when a node's properties are changed, or when nodes are connected or disconnected, and may allow users to inspect the data at each node or connection, either by hovering over it or through some other UI element.

In an embodiment users can often execute the entire workflow/pipeline or only selected parts of it. The system may also offer "debug" modes, where the workflow can be executed step-by-step, pausing at each node to inspect the state of the workflow. Nodes can often be grouped into sub-graphs or "meta-nodes" or "group nodes" encapsulating a set of operations into a single, reusable node. The system may allow users to save and import these meta-nodes or entire workflows, promoting reusability. The node-based interface is designed to make it easier to build and understand complex processes, often allowing users to do so without writing any code, using drop down menus, spreadsheets, tables or similar methods.

In an embodiment, node-based interfaces are novel to the process of generating planning structures for radiation therapy. In radiation therapy planning, various methods, options and interfaces exist for generating planning structures based on contoured organs and target volumes. The methods can range from straightforward expansions to more complex derived structures.

In an embodiment node-based operations may include margin expansions, Boolean operations, derived structures, and algorithmic methods. Margin expansions may include a uniform expansion operation to expand the contour of the treatment area uniformly in all directions by a fixed margin, and anisotropic expansion operations to expand the contour of the treatment area differently in specified directions.

Boolean operations may include a union operation to combining two or more structures to create a new, larger structure, an intersection operation to create a new structure based on the overlapping volume of two or more structures, a subtraction operation to remove the volume of one structure from another, an exclusion or crop operation to exclude areas of one structure from another in order to protect it from receiving high radiation doses, and superior/inferior structure extent limitation operation to limit a structure's superior or inferior extent by removing portions of a structure based on its location or distance from a reference structure.

Derived structures may include one or more ring structures that may be created around a target volume to help manage dose gradient, avoidance structures comprising artificial structures that may be made to avoid radiation in specific areas, often generated by offsetting from critical structures, dose painting structures which are custom-designed structures that guide dose delivery in a way that differs from the underlying anatomical structures, and shell or ring structures that may create a shell around organs-at-risk (OARs) to limit the dose that penetrates beyond the contour.

Algorithmic methods may include threshold-based methods in which structures that are generated or modified to be limited based on intensity values in the captured image. Various planning systems may offer different subsets of these options, and clinical guidelines may also influence which methods are most appropriate for a given case. The following are some non-limiting examples of components and tasks used in a node-based interface for planning structure generation.

In an embodiment, components of the node-based planning system may include nodes, edges/links/connections, a canvas or workspace GUI, a toolbar or sidebar, and functional operations.

In non-limiting examples, nodes may include Margin Expansion Nodes (Uniform and Anisotropic), Boolean Operation Nodes (Union, Intersection, Subtraction, Exclusion), Derived Structure Nodes (Ring, Avoidance, Dose Painting, Shell), Algorithmic Method Nodes (Threshold-based), Smoothing Nodes (reduce sudden changes in shape along the structure edge), and Utility nodes—Inspector, data split, data combine. Ports may include Input ports for receiving contour, structure data, output of previous nodes, Output ports for sending the modified or created structures, where Ports can accept single or multiple inputs, depending on the specifics of the node. Ports output multiple connections, which facilitates node reuse in the flow as well as allows for inspection during the flow creation. Properties or parameters may include margin values for expansion nodes, selection of structures for boolean operations, settings for derived structures, and threshold values for algorithmic methods.

The Boolean operations node performs Boolean operations as binary operations that work on tow input structures to produce a single output structure. In a non-limiting example, the union operation combines two input structures into a single output structure that includes the entire area or volume of both inputs. This operation is equivalent to the logical "OR" operation. The union operation may take as input two structures. As output the resulting structure contains all the areas or volumes covered by the input structures. While the union operation is defined for two inputs, the operation can be extended to multiple structures by sequentially applying the Union operation. For example, combining structures A, B, and C can be done by first combining A and B into D, then combining D with C to produce the final output.

In a non-limiting example, the Intersection operation creates an output structure that represents the area or volume shared by both input structures. This operation is equivalent to the logical "AND" operation. The intersection operation may take as input two structures. The output structure consists of the overlapping area or volume shared by the two input structures. If no overlap exists, the output structure is empty.

In a non-limiting example, the Crop operation subtracts the area or volume of one structure from another. This operation is useful for isolating or removing specific regions of a contour or structure. The input consists of structure A, the structure to be cropped, and structure B, the structure defining the subtraction area/volume. The output structure is the portion of A that does not intersect with B. If A and B do not intersect, the output is the entirety of A. If A is fully contained within B, the output is empty.

In a non-limiting example, the Exclusive OR node (XOR) operation creates an output structure representing the area or volume that is present in either of the input structures but not in both. This operation is often used to highlight differences between two structures. The output structure includes the areas or volumes that are unique to each input structure. If the structures do not intersect, the output is the same as the Union of A and B. If the structures are identical, the output is empty.

The node-based planning system may include directional links from output to input ports, defining the workflow. Data types carried could include contour data, logical flags for boolean operations, or numeric values for thresholds.

In an embodiment, the node-based planning system may include a GUI having a canvas that is utilized as a workspace for users to direct planning operations. The canvas GUI may include a large, scrollable, and zoomable space where the nodes and connections are laid out. The toolbar, or sidebar, may contain a list of available nodes and additional tools for zooming, saving, or loading workflows.

The node-based planning system provides functions such as drag-and-drop which permits dragging nodes from the sidebar and making connections, real-time feedback to permit real-time visualization updates as each node is configured and connected, data inspection which permits hovering over a node or connection could reveal contour shapes, dimensions, or summary statistics, execution control providing an option to execute the entire workflow or just selected nodes, modularity and reusability comprising one or more meta-nodes that may encapsulate common sets of operations in which workflows can be saved and imported, and templating and standardization in which Common or standardized planning structures and derived structures can be made available via a library or browser interface which can be loaded into the node interface and subsequently edited or modified and saved.

By combining multiple nodes, these detailed arrangements allow medical physicists and other clinicians to visually and interactively construct complex workflows for radiation therapy planning. The node-based interface would support robust, nuanced planning structures while providing real-time feedback and modularity, leading to efficient and effective treatment planning.

Storing and applying node-based workflows for later use can be an effective way to standardize processes, save time, and ensure consistent quality, especially in complex tasks like planning structure generation for radiation therapy.

Storing node-based workflows permits workflow operations such as serialization, metadata operations, storage operations, and user interface options. In serialization, after a user constructs a workflow within the node-based interface, this workflow can be serialized into a data format such as XML or JSON or other scripting computer language. Serialization captures every detail of the workflow, including the types of nodes used, their parameters, and the connections between them. Along with the serialized workflow, metadata can be added to give a description, specify use-cases, or provide other contextual information. This makes it easier to search for and identify the purpose of each stored workflow later on. These serialized workflows, along with the attached metadata, can be stored in a centralized database. This database might be cloud-based for accessibility or could exist within a local network depending on the security requirements. Within the node-based interface, buttons or menu options can be integrated for "Save as Template" or "Load Template," enabling users to easily store or retrieve workflows.

In an embodiment stored node-based workflows may be applied to operations. These stored node-based workflows may be retrieved and utilized by the system. In non-limiting examples, these operations may include:

1. Template Discovery: When a user needs to perform a task that a stored workflow could assist with, they can search the database for suitable templates. A good search interface might allow filtering based on metadata attributes like "treatment type," "organ involved," or "creator."
2. Preview and Import: After identifying a promising workflow, users can preview it to understand its structure and functionality. If it suits their needs, they can import this workflow into their current workspace.
3. Customization: Although the imported workflow serves as a starting point, users can modify nodes, add new nodes, or remove existing nodes to better adapt the workflow to the specific task at hand.
4. Validation: Before execution, particularly in critical applications like medical treatment planning, the workflow should be validated to ensure it will produce the desired results. This might involve a dry-run with simulated or historical data.
5. Execution: Once validated, the workflow can be executed to produce the desired output. In the case of radiation therapy planning, this would result in the generation of relevant planning structures.
6. Option to Save as New Template: After customization and successful execution, users can opt to save the modified workflow as a new template for future use, complete with its own set of metadata.
7. Activity Logging: For quality assurance and compliance, activities like template application and modifications can be logged.

By using this approach, the expertise and effort invested in creating a complex node-based workflow can be captured, stored, and reused, optimizing efficiency and consistency across similar tasks or projects.

In an embodiment a number of nodes have been created to provide efficient operations for the design and implementation of radiation treatment plans utilizing the image data captured from one or more image scans. Algorithmic nodes provide both threshold and general processing of medical images. An algorithmic threshold node processes medical images associated with a contour set, such as CT or MR scans, where the contours are anatomically aligned to the images. The primary function of this node is to apply a threshold to the image intensity values within the defined contour, producing a modified contour that represents the voxels within the specified intensity range.

The algorithmic threshold node receives as input a 2D or 3D contour and a range of image intensity values specified by low and high thresholds. The medical image associated with the contour (e.g., CT or MR scan) is converted to intensity units, such as Hounsfield units for CT scans, prior to the thresholding operation. The contour defines the boundary within which the thresholding operation is applied. Only the pixels or voxels within this boundary are considered. For each voxel within the contour boundary, the intensity value of the underlying image voxel is compared against the specified threshold range. If the voxel's intensity value falls within the threshold range, it is retained; otherwise, it is discarded.

To regenerate the contour for the image, a new contour is generated based on the retained voxels that meet the threshold criteria. The resulting contour represents the area or volume where the image intensity falls within the specified range. As output to the user, typically a Radiologist or Radiation oncologist, the modified contour, representing the voxels that lie within the intensity range within the bounds of the desired threshold, is output from the node. This operation allows for precise manipulation of medical images based on specific intensity values, aiding in the segmentation and analysis of regions of interest within the anatomical structures.

A general algorithm node is a versatile operation designed to adapt to a variety of algorithmic processes for modifying input contours or structures. This node can incorporate machine learning models or specific algorithms to transform the input in a manner tailored to a particular task or objective in medical imaging.

In an embodiment, the algorithm node receives as input medical image data comprising contours or structures, which may be represented as either 2D or 3D segmentation masks or polygons. The algorithm node is capable of applying a range of algorithmic operations to the input. These operations can be predetermined or dynamically chosen based on the specific task. As non-limiting examples, Machine Learning Models: The node can integrate trained machine learning models that predict and modify the input contours based on learned features from similar medical images, and Specific Algorithms: The node can apply traditional image processing or computational geometry algorithms, such as edge detection, thresholding, or custom contour alterations, to achieve the desired modification.

The algorithm node is designed to be flexible, allowing for the selection or adjustment of the algorithm based on the task at hand. This might include tasks such as improving the accuracy of contour delineation, enhancing image segmentation, or adjusting the shape of anatomical structures for further analysis. The node can also provide feedback mechanisms to refine the algorithmic operation, ensuring the output meets clinical or technical standards. The output of the node is a modified contour or structure, represented in the same format as the input. The output reflects the specific algorithmic modification applied, whether derived from a machine learning model or another computational method.

In an embodiment, a node-based interface can be used to generate and manipulate treatment planning structures for prostate cancer. By using various nodes such as Margin Expansion, Boolean Operations, Derived Structures, and Algorithmic Methods, clinicians can visually and interactively create complex workflows. This system offers modularity, real-time feedback, and the ability to save and reuse workflows, ensuring efficient and accurate treatment planning.

In a non-limiting example, the node-based system could be used to generate treatment planning structures for treatment of prostate cancer. In this example the primary target volume could be represented by the prostate structure as captured in medical imaging data. Adjacent structures that are often included in prostate cancer treatment include the seminal vesicles. An Organ-at-Risk (OAR) in this scenario could be the rectum, an OAR located posteriorly to the prostate, bladder superiorly and anteriorly to the prostate, and femoral heads laterally to the prostate.

In this non-limiting example, if the user wished to expand the margin of the planning area the user could perform this action through the use of a union node, a uniform expansion node, and an anisotropic expansion node. If a union node is used to expand the area to include the prostate and seminal vesicles, before expanding the prostate to create the CTV, the user first combines the prostate and seminal vesicles using a "Union" node. This union creates a combined structure that includes both the prostate and seminal vesicles. To perform this operation, the user drags the "Union" node into the workspace, connects it to both the "Prostate" and "Seminal Vesicles" nodes, and generates a new combined structure "Combined Prostate plus Seminal Vesicles".

A "Uniform Expansion" node is added next. The combined prostate and seminal vesicles structure is input into this node, and a 5 mm expansion is applied uniformly in all directions to generate the Clinical Target Volume (CTV). The user connects the "Combined Prostate plus Seminal Vesicles" node to a "Uniform Expansion" node and sets the margin to 5 mm. An "Anisotropic Expansion" node may then be used to expand the CTV by 5 mm anterior-posteriorly, 4 mm laterally, and 3 mm superior-inferiorly, creating the Planning Target Volume (PTV).

The user may then utilize one or more Boolean operation nodes to modify the PTV and update the treatment plan. Creating an overlap volume may use an "Intersection" node to identify the overlap between the PTV and rectum, helping to evaluate potential high-dose regions. The user may connect the PTV and Rectum nodes to an "Intersection" node.

To identify the rectum area outside the high-dose region, a "Subtraction" node may be used to subtract the PTV from the rectum. The user links the Rectum and PTV nodes to a "Subtraction" node. To spare the bladder from being included in the PTV A "Crop" node may be applied to exclude the superior portion of the bladder that overlaps with the PTV, protecting it from high radiation doses. The user may add this node and connect it to the Rectum and PTV nodes, limiting the extent as specified.

Other modifications to the PTV may be accomplished through the use of derived structures compiled from combining more than one operational node. In this example A "Ring Structure" node is used to create a 5 mm ring around the PTV to manage the dose gradient. The user may drag a "Ring Structure" node into the workspace and connect it to the PTV node. Avoiding inclusion of the femoral heads in the PTV may be accomplished through the use of an avoidance structure node. The user generates an avoidance structure around the femoral heads using an "Avoidance Structure" node, offset by 10 mm.

Modifications to the dosage delivered through the use of a "Dose Painting" node to customize dose delivery within the PTV based on imaging data, creating a high-dose region. The user connects the PTV and imaging data nodes to the "Dose Painting" node to create the high-dose region. Additionally, to avoid harming the rectum the user may create a shell around the rectum with a 3 mm thickness using a "Shell Structure" node to limit dose penetration. The user adds a "Shell Structure" node and connects it to the Rectum node.

Additionally, a "Threshold-Based Method" node may be used to generate a structure that excludes boney anatomy based on CT intensity thresholds. The user may connect the CT image node to a "Threshold-Based Method" node, which is then configured for bone segmentation to accomplish this boney anatomy exclusion.

Turning now to FIG. 1, presents a process flow diagram of the edge node creation elements consistent with certain embodiments of the present invention is shown. At 100 one or more input structures are retrieved and presented to the operation node 102. The operation node 102 analyzes the input structures to identify the node parameters that define the edges. The operation node 102 provides the process step that produces the desired output 104.

Figure 2:
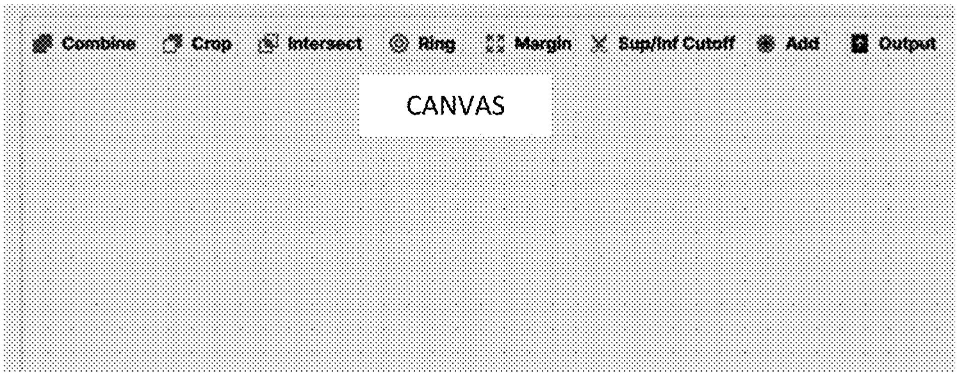
FIG. 2 is a component diagram of the user interface canvas consistent with certain embodiments of the present invention.

Turning now to FIG. 2, presents a component diagram of the user interface canvas consistent with certain embodiments of the present invention is shown. The Graphical User Interface (GUI) presents a canvas 200 to permit users to identify and combine operations in a graphical manner permitting the design of a treatment plan without the need to create new code to create the operations plan for treatment.

Figure 3:
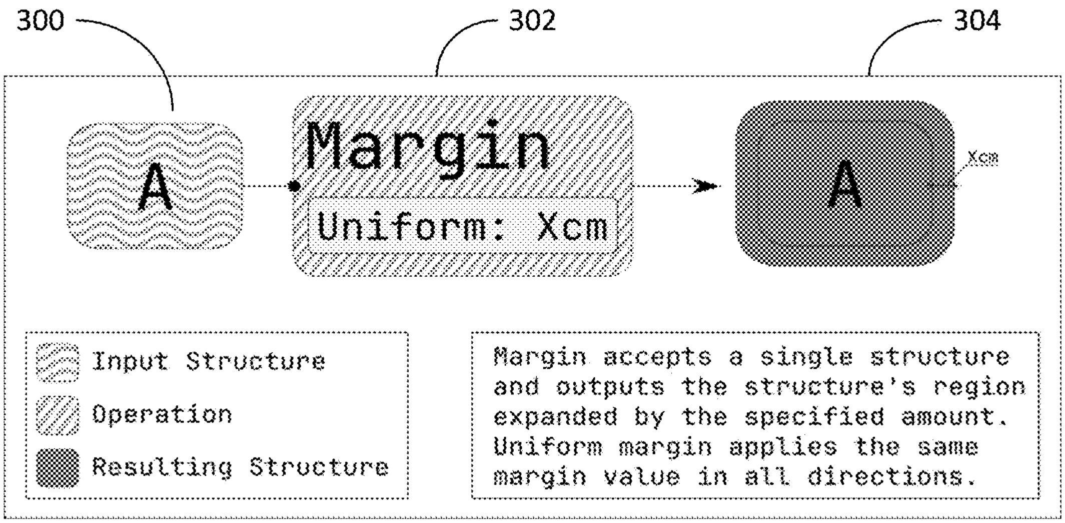
FIG. 3 is a component operation diagram for the uniform Margin node operation consistent with certain embodiments of the present invention.

Turning now to FIG. 3, presents a component operation diagram for the uniform Margin node operation consistent with certain embodiments of the present invention is shown. In a uniform Margin operation if a single value is provided, the structure's surface is uniformly expanded or contracted by moving the surface outward or inward by the specified amount along all dimensions. At 300, the operation takes as input either a 2D contour or a 3D structure containing margin value as a parameter. At 302 the margin value, which dictates the degree of expansion or contraction, can be provided as a single numerical value, resulting in a uniform margin that affects all dimensions equally. Positive margin values indicate expansion, while negative values indicate contraction of the structure. If a single value is provided, the structure's surface is uniformly expanded or contracted by moving the surface outward or inward by the specified amount along all dimensions. Given that structures can have arbitrary shapes with faces or edges that may not align perfectly with the margin directions, the operation includes an interpolation step. This step ensures that the entire surface of the structure is modified smoothly, even in areas where the geometry is complex or irregular.

The operation modifies the input structure by moving its surface based on the provided margin values. This modification is applied to all relevant sections of the structure, including intermediate-facing sections that are interpolated to ensure continuity and smoothness. At 304, the output of the operation is a modified contour or 3D structure that reflects the applied margin, whether uniform or nonuniform. The new structure maintains the overall shape of the original input but adjusted according to the specified margin.

Figure 4:
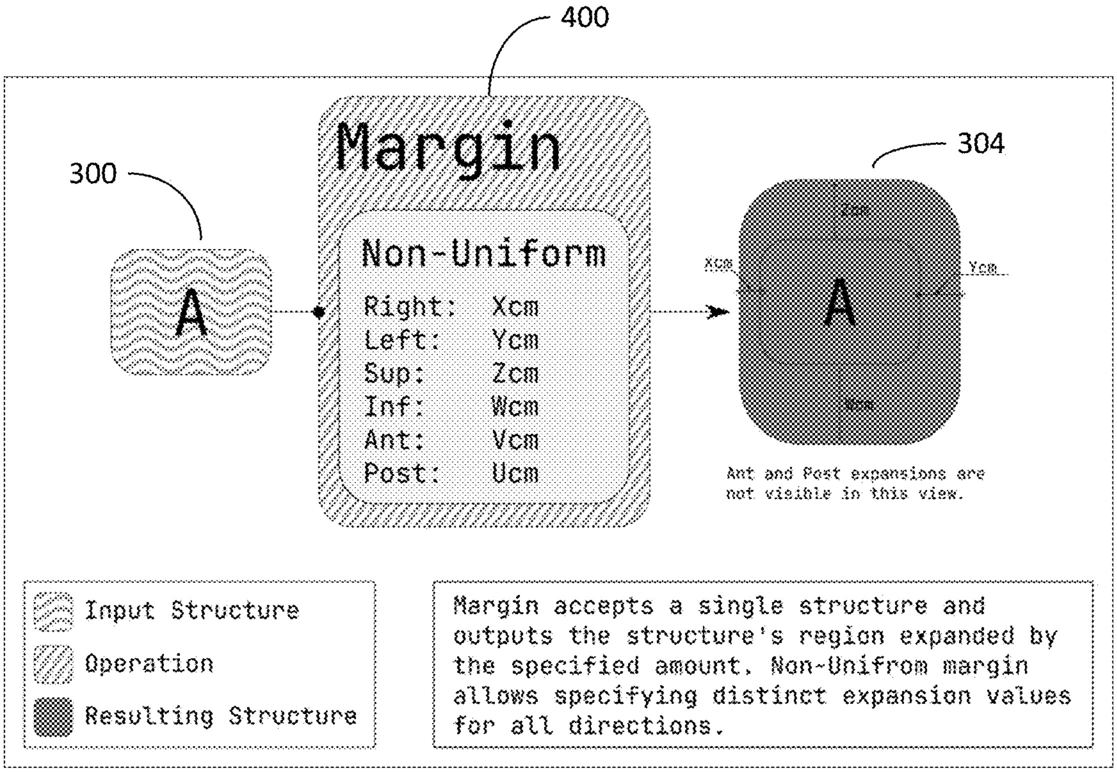
FIG. 4 is a component operation diagram for the non-uniform Margin node operation consistent with certain embodiments of the present invention.

Turning now to FIG. 4, presents a component operation diagram for the non-uniform Margin node operation consistent with certain embodiments of the present invention is shown. In a non-uniform Margin operation if multiple values are provided, the structure's surface is expanded or contracted differently along each specified dimension. This allows for complex modifications, accommodating the unique anatomical features of the input structure. At 300, the operation takes as input either a 2D contour or a 3D structure containing margin value as a parameter. At 400 the margin value, which dictates the degree of expansion or contraction, can be provided as multiple numerical values, allowing for a nonuniform margin with different expansions or contractions along different dimensions. Positive margin values indicate expansion, while negative values indicate contraction of the structure. If multiple values are provided, the structure's surface is expanded or contracted differently along each specified dimension. This allows for complex modifications, accommodating the unique anatomical features of the input structure. Given that structures can have arbitrary shapes with faces or edges that may not align perfectly with the margin directions, the operation includes an interpolation step. This step ensures that the entire surface of the structure is modified smoothly, even in areas where the geometry is complex or irregular.

The operation modifies the input structure by moving its surface based on the provided margin values. This modification is applied to all relevant sections of the structure, including intermediate-facing sections that are interpolated to ensure continuity and smoothness. At 304, the output of the operation is a modified contour or 3D structure that reflects the applied margin, whether uniform or nonuniform. The new structure maintains the overall shape of the original input but adjusted according to the specified margin.

Figure 5:
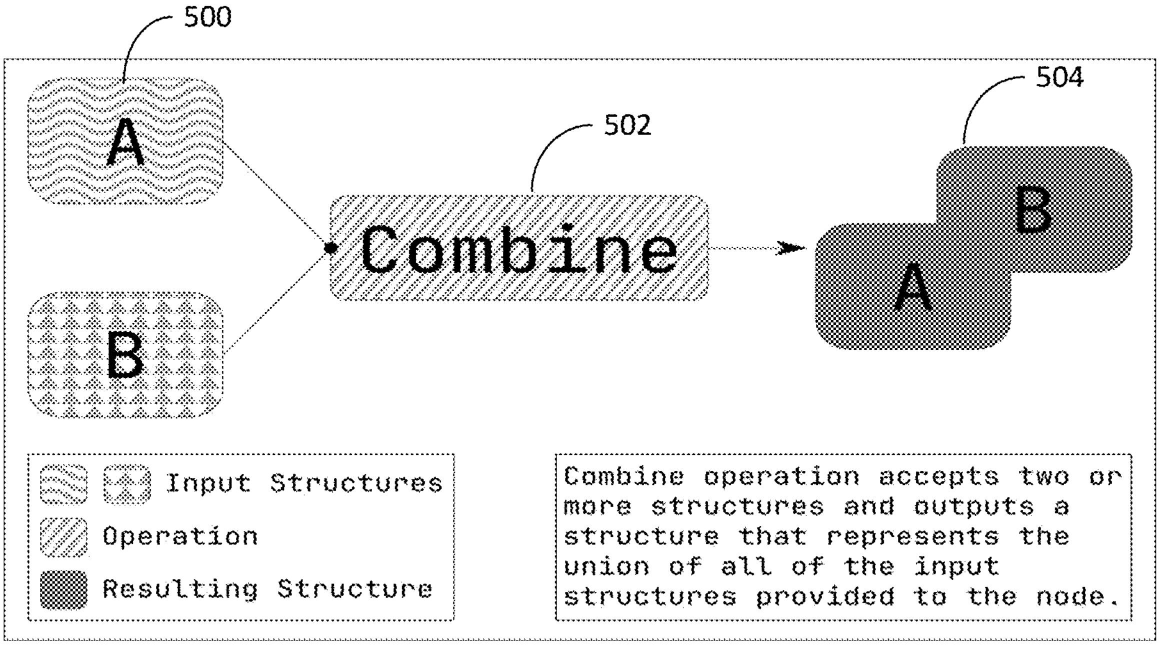
FIG. 5 is a component operation diagram for the Combine node operation consistent with certain embodiments of the present invention.

Turning now to FIG. 5, presents a component operation diagram for the Combine node operation consistent with certain embodiments of the present invention is shown. At 500 the combine operation accepts two or more input structures. At 502 the Combine operation overlays the image boundaries of each input structure. At 504 the output structure from the Combine operation represents the union of all of the input structures provided as input to the Combine node.

Figure 6:
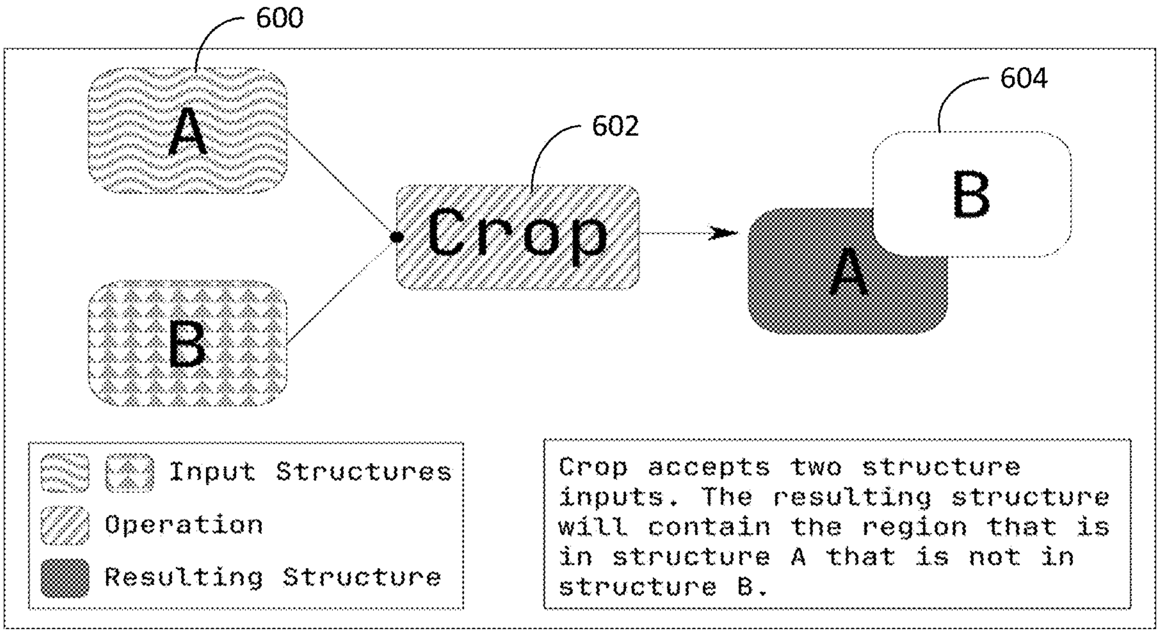
FIG. 6 is a component operation diagram for the Crop node operation consistent with certain embodiments of the present invention.

Turning now to FIG. 6, presents a component operation diagram for the Crop node operation consistent with certain embodiments of the present invention is shown. At 600 the combine operation accepts two input structures. At 602 the Crop operation overlaps the two input structures to overlay the image boundaries of each input structure. At 604 the output structure will contain the region that is in structure A that is not in structure B.

Figure 7:
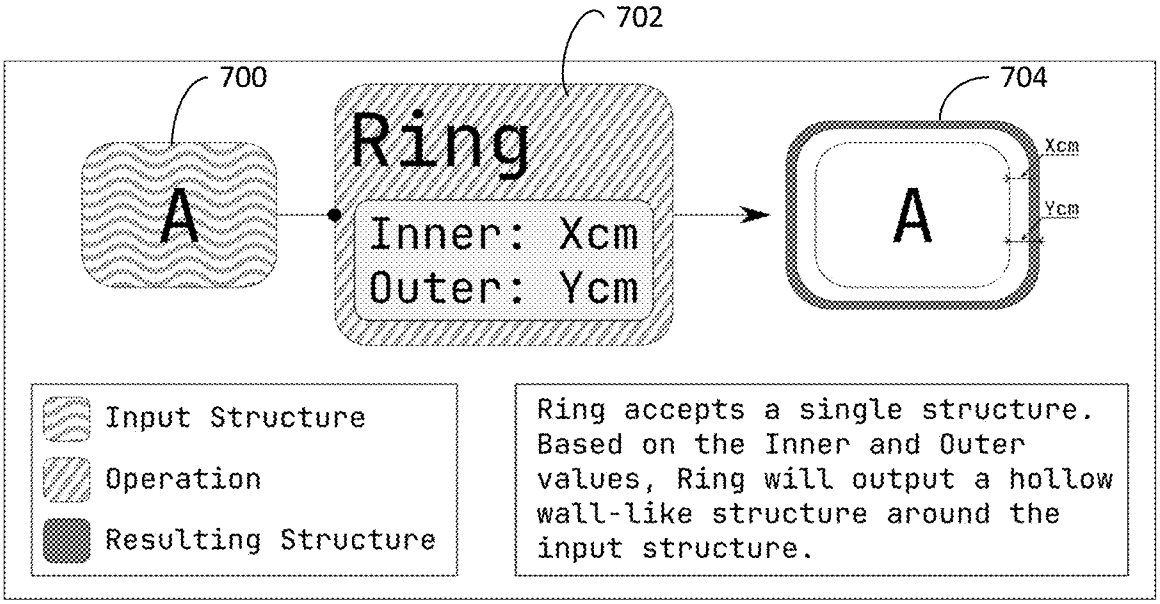
FIG. 7 is a component operation diagram for the Ring node operation consistent with certain embodiments of the present invention.

Turning now to FIG. 7, presents a component operation diagram for the Ring node operation consistent with certain embodiments of the present invention is shown. The Ring Operation is designed to generate a hollow structure around an input structure by applying predefined inner and outer offsets. At 700 The input to the operation is a single structure, which can be represented in either 2D or 3D formats, such as segmentation masks or polygons. At 702 the Ring operation utilizes Inner and Outer offsets to create the boundaries of the operation. Inner Offset: This parameter defines the distance between the surface of the input structure and the inner surface of the resulting hollow structure. A positive inner offset results in an inner surface that is inside the input structure, while a negative inner offset positions the inner surface outside the original boundaries. Outer Offset: This parameter defines the distance between the surface of the input structure and the outer surface of the resulting hollow structure. A positive outer offset creates an outer surface that is outside the input structure, while a negative outer offset positions the outer surface inside the original boundaries.

The structure modification operation calculates the positions of the inner and outer surfaces based on the provided offsets. The resulting structure is hollow, with the area or volume between the inner and outer surfaces representing the "ring." If both offsets are positive, the ring fully surrounds the input structure. If one or both offsets are negative, the ring may intersect with or partially overlap the input structure.

At 704 The output of the Ring Operation is a new structure that is hollow, with its boundaries defined by the inner and outer offset distances relative to the original input structure. The resulting structure is provided in the same format as the input (either 2D or 3D segmentation masks or polygons).

Figure 8:
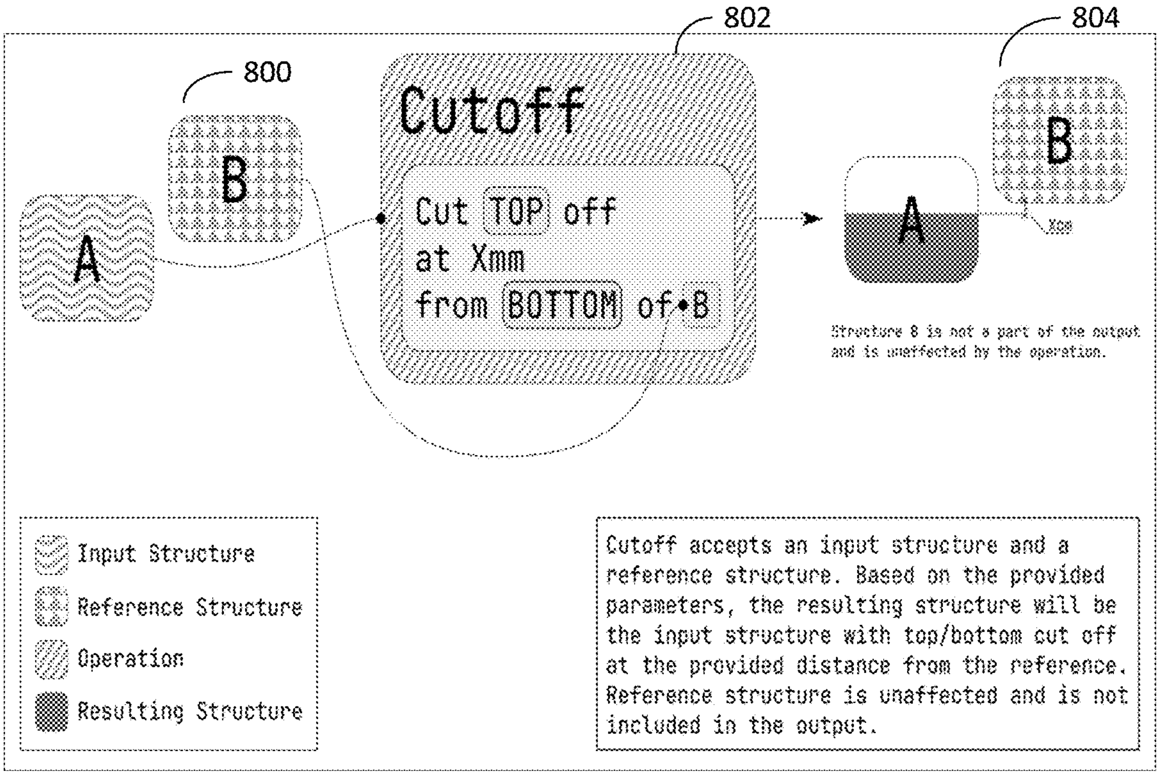
FIG. 8 is a component operation diagram for the Cutoff node operation consistent with certain embodiments of the present invention.

Turning now to FIG. 8, presents a component operation diagram for the Cutoff node operation consistent with certain embodiments of the present invention is shown. The Smoothing Node is designed to refine and smooth the shape of input contours by applying a variety of polygon or contour-shape smoothing techniques. At 800 the Cutoff node accepts an input structure and a reference structure. At 802 the Cutoff node operation removes a specified portion from the input structure, such as the top portion of the first structure, and removes a specified portion from the input structure. Based upon parameters provided by a user such as, in a non-limiting example, cut the top off at a set distance of the input structure and cut the bottom off of the input structure. The output at 804 produces the input structure with the top and bottom cut off, but the reference structure is unaffected and is not included in the output.

Figure 9:
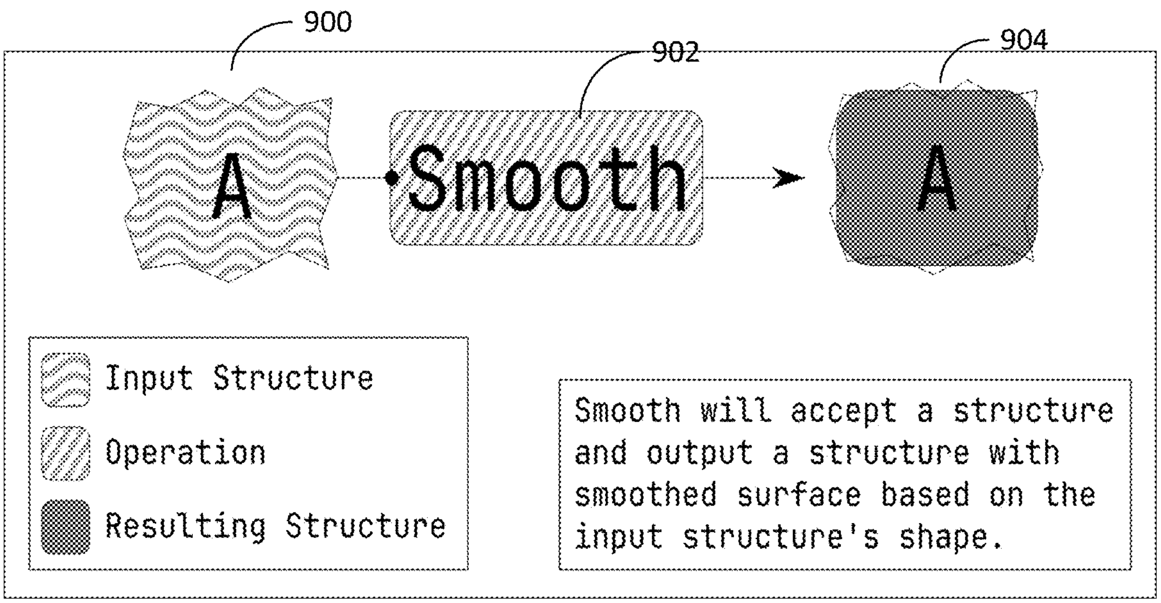
FIG. 9 is a component operation diagram for the Smooth node operation consistent with certain embodiments of the present invention.

Turning now to FIG. 9, presents is a component operation diagram for the Smooth node operation consistent with certain embodiments of the present invention is shown. The Smoothing Node is designed to refine and smooth the shape of input contours by applying a variety of polygon or contour-shape smoothing techniques. At 900 The node accepts contours as input, which can be represented in either 2D or 3D formats, such as segmentation masks or polygons. At 902 The Smoothing Node may utilize a range of contour-shape smoothing methods to refine the input contours. One exemplary method involves applying a weighted moving average to the points along the contour border. A weighted moving average involves calculating an average position for each point on the contour, considering the positions of neighboring points. Weights are assigned to these neighboring points to control the influence they have on the averaged position. The smoothing node process smooths the contour by reducing sharp angles and irregularities, leading to a more consistent and rounded representation. Additionally, the smoothing process can be applied successively in iterations, progressively refining the contour shape with each pass. This ensures that the final contour is free of unwanted noise or distortions while maintaining the overall anatomical accuracy.

At 904 the output of the node is a smoothed contour, where each point on the contour represents an averaged position derived from the smoothing process. The resulting contour is output in the same representation format as the input (either 2D or 3D segmentation masks or polygons), ensuring seamless integration into subsequent processing steps.

Figure 10:
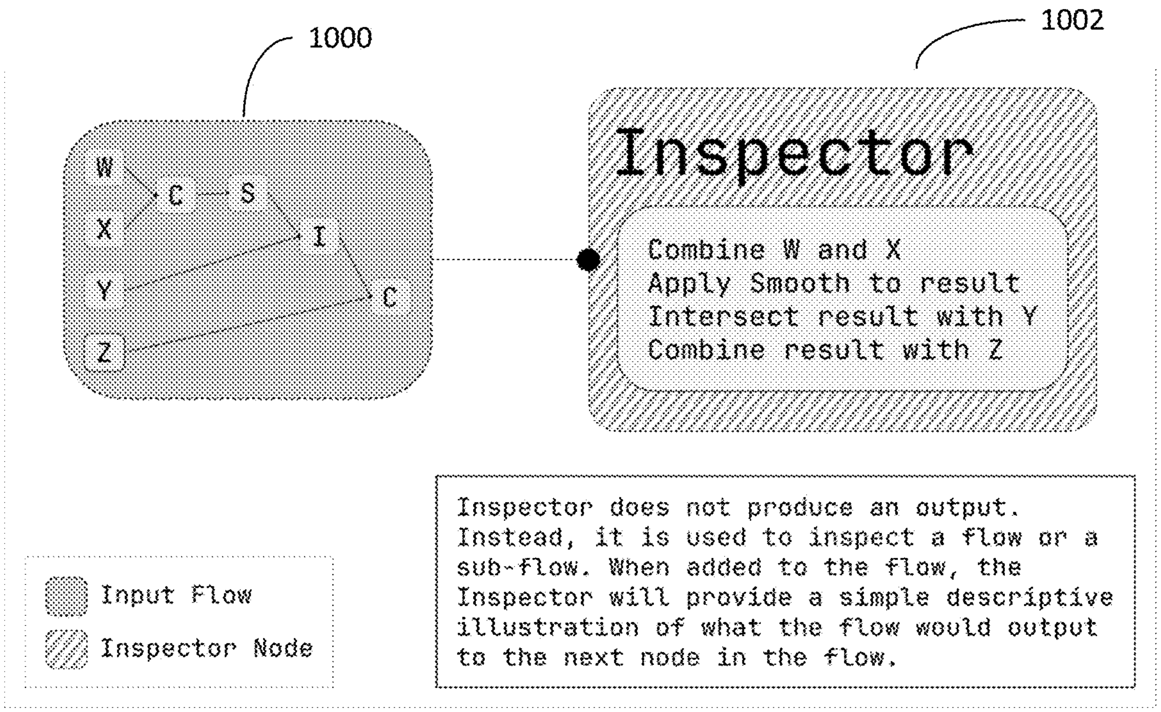
FIG. 10 is a component operation diagram for the Inspector node operation consistent with certain embodiments of the present invention.

Turning now to FIG. 10, presents a component operation diagram for the Inspector node operation consistent with certain embodiments of the present invention is shown. The Inspector Node is a specialized helper node within a node-based user interface (UI) designed for medical imaging workflows. Unlike other nodes that perform operations on structures, the Inspector Node serves as a tool for users to visualize and reason about the output that a node graph or a subset of it will produce upon execution. This node aids in debugging, planning, and refining complex workflows by providing real-time feedback as users interact with the node graph. At 1000 The Inspector Node can be inserted into any output of a graph node, allowing it to display and analyze the intermediate or final results of the operations planned in the graph. Alternatively, the Inspector Node can exist independently within the graph, not directly connected to any specific node output but still capable of visualizing the overall operations defined within the graph.

As users interact with and modify the node graph, the Inspector Node updates in real-time to reflect the planned operations. This allows users to immediately see how changes in the graph will affect the final output. The primary function of the Inspector Node is to visualize the data or structures that will result from the current configuration of the node graph. This visualization helps users understand the cumulative effect of the operations they have configured. In addition to visualization, the Inspector Node may provide analytical tools or metrics that help users evaluate the effectiveness or correctness of the planned operations. This can include summaries of the expected changes, comparisons between inputs and outputs, or other diagnostic information.

The Inspector Node enhances user interaction with the node graph by providing an intuitive and immediate way to assess the impact of changes. Users can explore different configurations, test hypotheses, and refine their workflow without needing to execute the entire graph to see the outcome. The node's visual and analytical feedback guides users in optimizing the workflow for their specific needs, ensuring that the final output meets their requirements.

At 1002 the inspector node outputs a visual or analytical representation of the potential outcome based on the current state of the node graph. This output is intended for user interpretation and decision-making rather than direct manipulation of medical imaging data.

Figure 11:
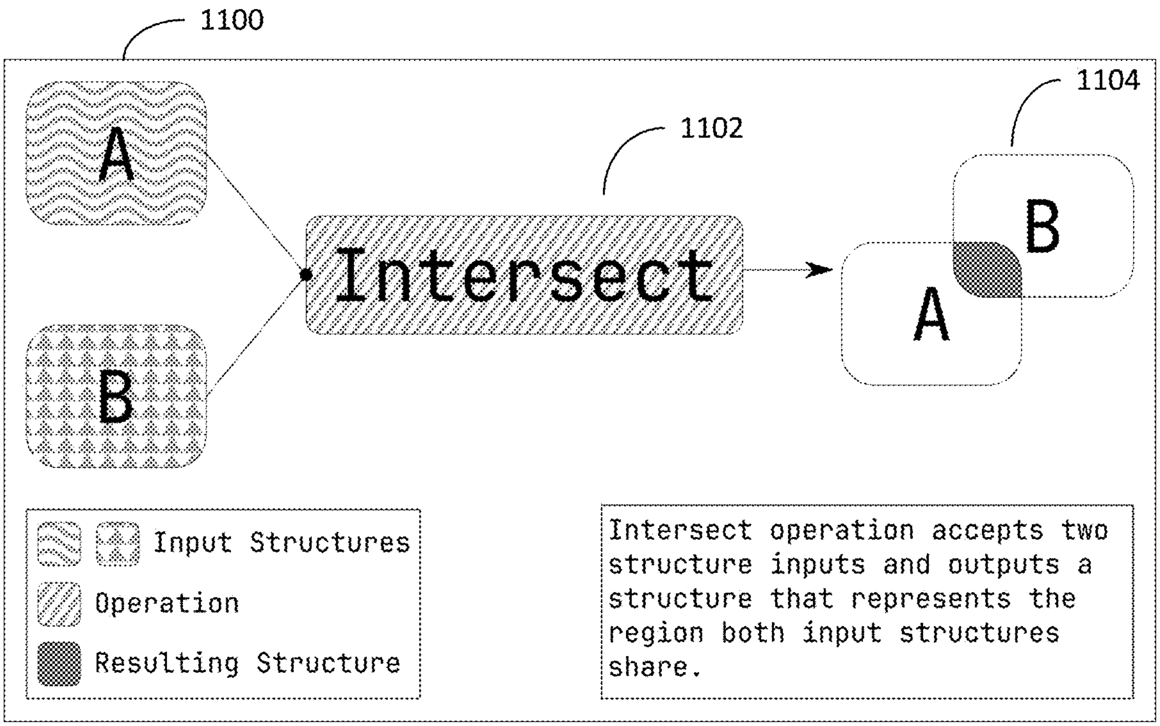
FIG. 11 is a component operation diagram for the Intersect node operation consistent with certain embodiments of the present invention.

Turning now to FIG. 11, presents a component operation diagram for the Intersect node operation consistent with certain embodiments of the present invention is shown. The Intersection operation creates an output structure that represents the area or volume shared by both input structures. This operation is equivalent to the logical "AND" operation. The intersect node at 1100 receives a plurality of input structures defining regions within the image data that may be used for radiation treatment planning. Each structure is bounded by defined limits of the regions within the image data. At 1102 the intersect node overlays the bounded regions and presents as output at 1104 the region that both input structures share based upon the defined boundaries of the input regions. If no overlap exists for the input structures, the output structure is empty.

The invention claimed is:

1. A system for radiation treatment therapy planning, comprising:

a data processor receiving a set of imaging data;

said data processor further comprising a Graphical User Interface (GUI) active to provide images found within said set of imaging data and to provide interaction with said images to one or more medical practitioners;

one or more areas within said images identified as target volumes for radiation treatment and healthy organs and tissues;

said medical practitioners utilizing node-based functions to provide modifications to said one or more target volumes to identify Organs-at-Risk (OARs);

said data processor providing node-based functions as node-based operations that include margin expansions, Boolean operations, derived structures, and algorithmic methods;

said data processor updating said target volumes for radiation treatment and healthy organs and tissues with one or more of said medical practitioners provided modifications to create one or more original planned treatment volumes to be subject to radiation treatment therapy;

said data processor updating said one or more original planned treatment volumes utilizing said node-based operations to expand upon the original planned treatment volumes to generate more accurate specialized radiation treatment planning structures for said original planned treatment volume;

one or more of said medical practitioners approving a radiation treatment plan expressed in said specialized radiation treatment planning structures and storing said approved radiation treatment plan in electronic storage maintained within said data processor;

said data processor operative to optimize a radiation dose delivery for a particular patient based upon the generated specialized radiation treatment planning structures;

said data processor performing dosimetric verification analysis through the use of physical tests and computer simulations to increase confidence that the planned radiation dose delivery is accurately delivered by a treatment machine to be used to deliver radiation treatment therapy;

said data processor delivering said approved radiation treatment plan to said treatment machine where the treatment machine provides the radiation therapy expressed in the approved radiation treatment plan to said particular patient.

2. The system according to claim 1, where the GUI further comprises a canvas screen view permitting a user to drag-and-drop into said canvas screen view one or more nodes and connecting any one of said one or more nodes to any other node placed into said canvas screen.

3. The system according to claim 2, further comprising a plurality of nodes that perform actions or tasks to manage complex workflows, processes, or data pipelines by connecting different "nodes" together enabling the encapsulation of functions, operations, or tasks within nodes that can be visually connected to define a flow of data or control within said canvas screen view.

4. The system according to claim 1, where said medical practitioners are any of radiation oncologists, radiologists, or other radiation therapists.

5. The system according to claim 4, where said radiologist(s) and/or radiation oncologist(s) review the set of imaging data to identify critical structures, organs, and/or tumors that are present and visible within the imaging data.

6. The system according to claim 1, where said set of imaging data is acquired as a set of imaging data through the modalities such of Computer Tomography (CT), Magnetic Resonance Imaging (MRI), or Positron emission tomography (PET) scans.

7. The system according to claim 1, where said planned treatment volumes further comprise the Gross Tumor Volume (GTV), Clinical Tumor Volume (CTV), and the Planning Target Volume (PTV).

8. The system according to claim 7, where the Gross Tumor Volume (GTV), Clinical Tumor Volume (CTV), and the Planning Target Volume (PTV) define a tumor volume and the volumetric region for which radiation treatment is indicated and required.

9. The system according to claim 1, further comprising Machine Learning (ML) and Artificial Intelligence (AI) based algorithms utilizing deep learning and one or more trained data sets to generate treatment planning structures based upon learned patterns in the training data that have been reviewed and approved by one or more radiologists and/or radiation oncologists.

10. The system according to claim 1, where said node-based operations provide expansion of said target volumes uniformly in all directions by a fixed margin, expansion of the contour of said target volume in a non-uniform manner, combining two or more structures to create a new, larger structure within said target volume, and/or managing dose gradient for dose delivery to guide dose delivery in a way that differs from the underlying anatomical structure to limit the dose of radiation that penetrates beyond the defined contour of the treatment target volume.

* * * * *